(12) United States Patent
Leblans et al.

(10) Patent No.: US 6,512,240 B1
(45) Date of Patent: *Jan. 28, 2003

(54) METHOD AND APPARATUS FOR READING A RADIATION IMAGE THAT HAS BEEN STORED IN A PHOTOSTIMULABLE SCREEN

(75) Inventors: Paul Leblans, Kontich (BE); Luc Struye, Mortsel (BE)

(73) Assignee: Agfa-Gevaert, Mortsel (BE)

( * ) Notice: Subject to any disclaimer, the term of this patent is extended or adjusted under 35 U.S.C. 154(b) by 46 days.

This patent is subject to a terminal disclaimer.

(21) Appl. No.: 09/595,487

(22) Filed: Jun. 16, 2000

Related U.S. Application Data (60) Provisional application No. 60/142,276, filed on Jul. 2, 1999, and provisional application No. 60/159,004, filed on Oct. 8, 1999.

(51) Int. Cl.[7] .......................... A61B 6/00; G01N 23/04; G03C 5/16; G21K 4/00
(52) U.S. Cl. ....................................... 250/588; 250/581
(58) Field of Search ................... 250/581, 582, 250/588

(56) References Cited

U.S. PATENT DOCUMENTS

| | | | |
|---|---|---|---|
| 3,859,527 A | | 1/1975 | Luckey |
| 4,835,386 A | * | 5/1989 | Shimura et al. ............. 250/588 |
| 4,883,961 A | * | 11/1989 | Arakawa ..................... 250/588 |
| 5,028,509 A | | 7/1991 | Shimada et al. |
| 5,072,119 A | * | 12/1991 | Yamaguchi .................. 250/588 |
| 5,434,431 A | * | 7/1995 | Verbeke et al. ............. 250/588 |

FOREIGN PATENT DOCUMENTS

| | | | |
|---|---|---|---|
| EP | 0174875 | * 3/1986 | ........... C09K/11/61 |
| EP | 0 174 875 | 6/1990 | |

* cited by examiner

*Primary Examiner*—Georgia Epps
*Assistant Examiner*—Alicia Harrington
(74) *Attorney, Agent, or Firm*—John A. Merecki; Hoffman, Warnick & D'Alessandro (57) ABSTRACT

A radiation image read out method and apparatus including stimulating a divalent europium activated cesium halide phosphor screen wherein the halide is at least one of chloride and bromide, that has been exposed to a radiation image, detecting light emitted by the phosphor screen upon stimulation, and erasing the phosphor screen by exposing it to erasing light emitted by at least one laser source.

10 Claims, 5 Drawing Sheets

METHOD AND APPARATUS FOR READING A RADIATION IMAGE THAT HAS BEEN STORED IN A PHOTOSTIMULABLE SCREEN

This application claims the benefit of U.S. Prov. Appln. No. 60/142,276 filed Jul. 2, 1999 and Prov. Appln. No. 60/159,004 filed Oct. 8, 1999.

FIELD OF THE INVENTION

The present invention relates to method and a system for reading a radiation image that has been stored in a photostimulable phosphor screen. More particularly the invention relates to the re-use of the photostimulable phosphor screen.

BACKGROUND OF THE INVENTION

Radiation image recording systems wherein a radiation image is recorded on a photostimulable phosphor screen by exposing said screen to image-wise modulated penetrating radiation are widely used nowadays.

The recorded image is reproduced by stimulating the exposed photostimulable phosphor screen by means of stimulating radiation and by detecting the light that is emitted by the phosphor screen upon stimulation and converting the detected light into an electrical signal representation of the radiation image.

In such a system it is preferred, in view of economy, that the stimulable phosphor screen can be used in many imaging cycles.

The reuse of the stimulable phosphor screen is possible when the previously stored radiation image is erased to a sufficient extent.

When reading out an image by stimulating a phosphor screen that has been exposed to penetrating radiation, less than 90% of the stored energy is released. Thus there arises a problem that, upon reuse, part of the radiation image is still stored in the phosphor screen and can appear in the subsequent image as a so-called ghost image.

In general medical radiography, images are made with widely differing X-ray doses.

To make images of extremities, like e.g. fingers, doses are used of the order of 1 mR. On the other hand, images of internal organs, like the stomach are made with X-ray doses that may be as high as 300 mR.

To avoid ghosting, when making a 1 mR image immediately after a 300 mR image, the signal of the first image must be reduced by more than a factor of 300.

As a matter of fact, a dynamic range is desired in the second image of at least 100. This implies that the signal created by the first irradiation must be reduced by a factor of at least $3.10^4$, which is equivalent to requiring an erasure depth of $1/(3.10^4)=3.3.10^{-5}$.

According to U.S. Pat. No. 3,859,527 (column 4, lines 5–7) the phosphor can be reduced to neutral state by actions like a uniform illumination, irradiation or heating.

In commercial systems, the phosphor screen is erased by illumination with visible light. Incandescent lamps are commonly used because they are cheap, high power light sources.

High power is needed, because in order to guarantee a high through-put scanning system, the phosphor screen must be erased in a short time.

In the first place, high power lamps generate a lot of heat, which may destabilise the scanner to read out the storage phosphor screens. The size of the read out apparatus has to be rather large in order to enable removal of the heat generated by a powerful erasure unit which is required in order to have a high throughput. The more compact the read out apparatus, the more difficult it will be to remove the heat generated by a powerful erasure unit.

In the second place, an erasure unit containing incandescent lamps, like e.g. quartz halogen lamps, will be rather bulky because of the sockets that are needed to make a light source that illuminates the phosphor screen homogeneously.

In order to develop a reliable and compact storage phosphor screen digital radiography system it is important to reduce the power consumed by the erasure unit. This was not possible in the state of the art system without negatively affecting the throughput.

OBJECTS OF THE INVENTION

It is an object of the present invention to provide a method and a system for reading a radiation image that has been stored in a photostimulable phosphor screen wherein the screen is erased in between successive recordings to an adequate extent so as to permit re-use of the screen.

It is a further object of the present invention to provide such a system that is compact and has at the same time a high throughput.

Further objects will become apparent from the description given below.

SUMMARY OF THE INVENTION

The above mentioned objects are realised by a method having the specific features defined in claim 1.

Another aspect of the present invention relates to an apparatus for reading a radiation image that has been stored in a phosphor screen comprising a divalent europium activated cesium halide phosphor wherein said halide is at least one of chloride and bromide. The apparatus comprises a source of stimulating radiation arranged for emitting stimulating light, means for directing said stimulating light onto a photostimulable phosphor screen, a transducer for converting light emitted by said phosphor screen upon stimulation into an electrical signal and an erasing unit for erasing said photostimulable phosphor screen after having been stimulated. The erasing unit comprising at least one laser.

The term 'an erasing light source assembly' refers to either a single erasing light source or a group of more than one erasing light source. In the latter case when the electrical power is specified the value refers to the electrical power of the total assembly.

The present invention enables the use of a compact and low power erasure assembly without the need to increase the erasure time to an unacceptable extent. In this way the read out apparatus can be made very compact while its throughput is not negatively affected.

Still another aspect relates to a re-usable radiation detector comprising
- a photostimulable phosphor screen,
- at least one source of stimulating light arranged for stimulating said phosphor screen,
- an array of transducer elements arranged for capturing light emitted by the phosphor screen upon stimulation and for converting said light into an electrical signal representation,
- an erasing unit arranged for erasing said screen when it has been read out, means for transporting the phosphor screen and an assembly of stimulating light source(s), said array of transducer elements and said erasing unit relative to each other, an enclosure enclosing said photostimulable phosphor screen, said stimulating light source, said erasing unit, said array of transducer elements and said means for transporting the screen, interfacing means for communicating said electrical representation to an external signal processing device, wherein said erasing unit comprises at least one laser.

In one embodiment said stimulating light source and said erasing laser is the same light source.

Specific features for preferred embodiments of the invention are set out in the dependent claims.

In this document the term "radiation" has to be understood as any penetrating radiation and includes irradiation originating from a radioisotope (e.g. Co60, Ir192, Se75, etc.), radiation created by an X-ray generator of any type, radiation and high energy particles created by a high energy radiation generator (e.g. Betatron), radiation from a sample labeled with a radioisotope as is the case in e.g. autoradiography.

Further advantages and embodiments of the present invention will become apparent from the following description and drawings.

DETAILED DESCRIPTION OF THE INVENTION

Figure 1:
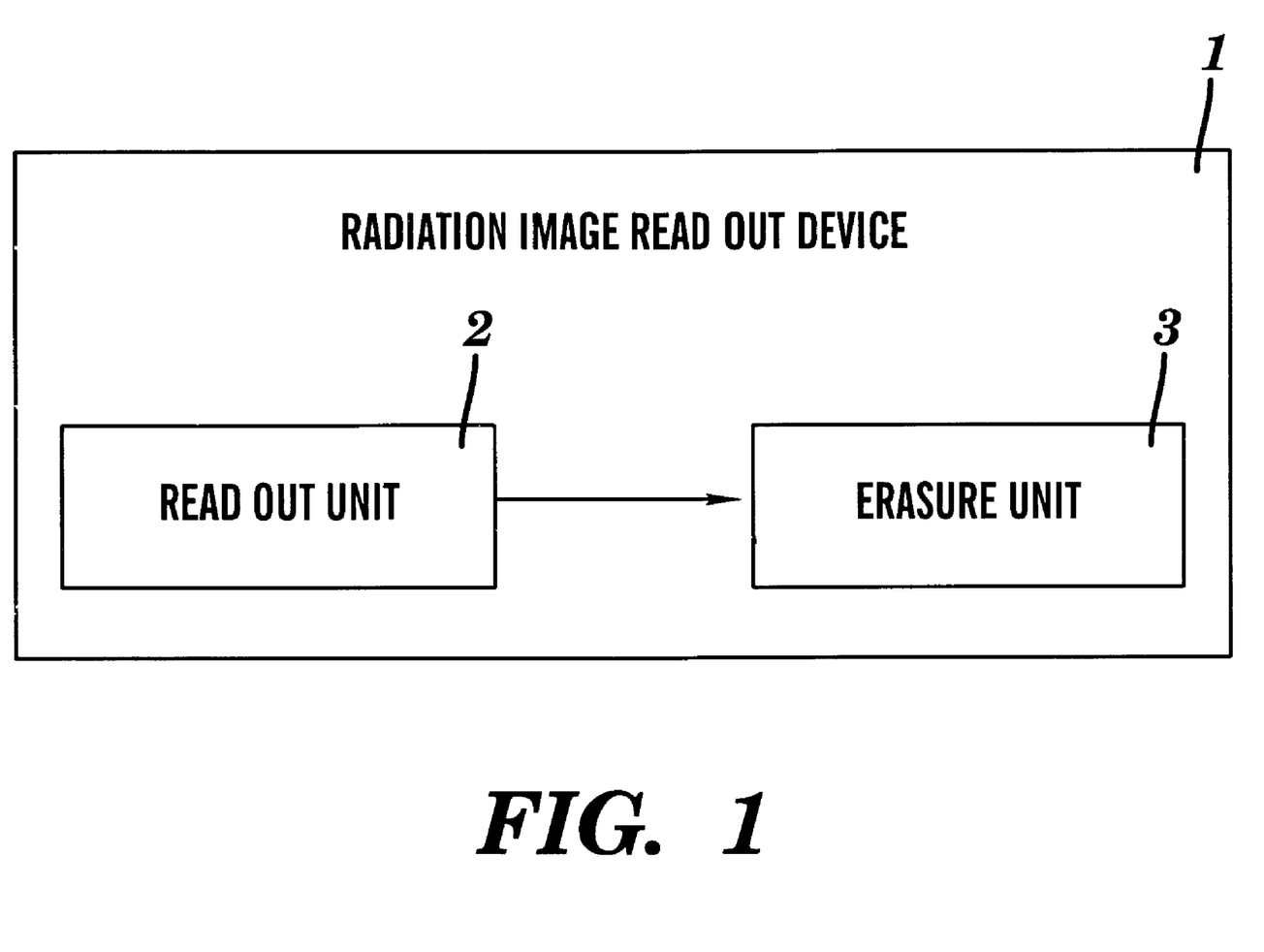
FIG. 1 is a block diagram representing the main components of an image read out apparatus comprising an erasure unit.

A radiation image read out device (1) according to the present invention is schematically shown in FIG. 1. The device generally comprises a image read out unit (2) and an erasure unit (3).

The read out and erasure units can be implemented as separate units or can be incorporated into a single unit.

First Embodiment

Figure 2:
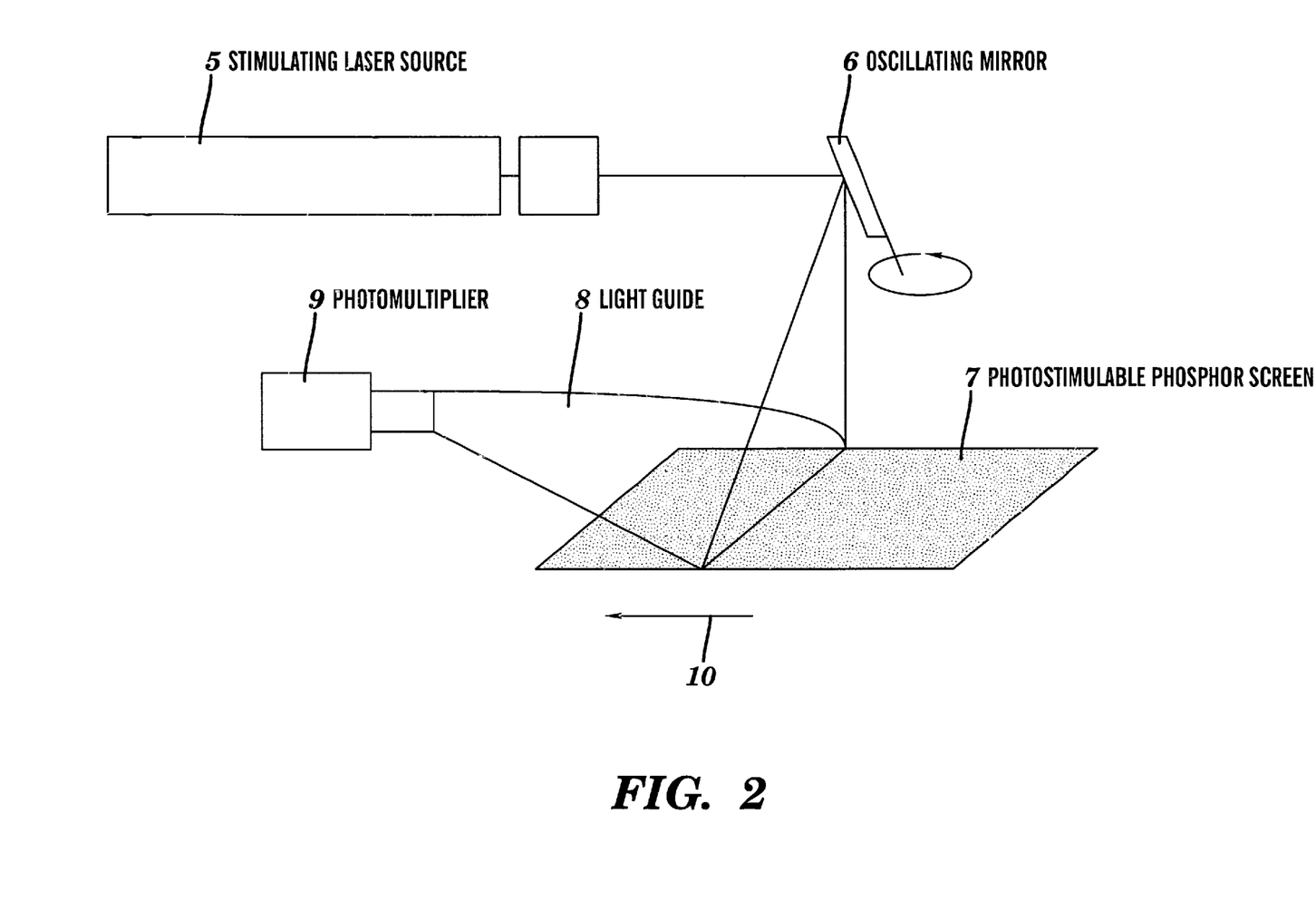
FIG. 2 shows an embodiment of a photostimulable phosphor read out unit of the flying spot type.

A first embodiment of an image read out unit is of the flying spot scanner type, this embodiment is shown in greater detail in FIG. 2.

The read out unit comprises a source of stimulating radiation (5), more particular a HeNe laser emitting light at 633 nm.

The unit further comprises an oscillating mirror (6) for deflecting light emitted by the stimulating laser source onto the photostimulabe phosphor screen (7) into the scan direction, a light guide (8) for guiding light emitted by the photostimulable phosphor screen upon stimulation onto a photomultiplier (9).

It will be clear that various alternatives for the components of the apparatus may be envisaged, e.g. the HeNe laser can be replaced by a diode laser emitting at a wavelength of between 600 and 700 nm, the oscillating mirror can be replaced by a multi-facet mirror etc.

A read out unit of the flying spot type is generally combined with an erasure unit that is optically separated from the read out unit so that there is no interference between read out and erasure. Read-out and erasure may take place simultaneously or, alternatively, erasure may start after completion of screen read-out. The photostimulable phosphor screen is transported through the read unit into the erasure unit. An image line which has been read out is subsequently erased.

If erasure and read-out of the screen take place simultaneously at different sections of the screen, the laser(s) in the erasure source must be optically separated from the read-out unit, to avoid interference of the erasing light with the stimulation light.

This can be achieved by placing the erasing laser(s) in a black casing. The inside of the erasure unit may be coated with e.g. black velvet, which very efficiently reduces reflection and transmission of erasure light in unwanted directions. Between the erasure unit and the read-out unit, black brushes may be placed. This allows transport of the storage phosphor screen from the read-out to the erasure unit, but efficiently blocks the light transmission between both units.

Alternatively, a set of black rollers is placed between the read-out and erasure units. If, during screen transport there is good contact between the screen and the rollers, light transmission from the erasure unit to the read-out unit is avoided.

Since the laser(s) in the erasure unit are not used for scanning, high power lasers with relatively large emitting dimensions, i.e. $10\mu$ or larger, can be used.

Lasers of this type are e.g.:

An SDL-3400 laser, that has emitting dimensions of 1 cm×1$\mu$ and a power of up to 20 W.

An SDL-7430 laser has a power of 0.5 W and emits at 680 nm.

Another type of high power laser is a fiber-coupled laser. This type of laser cannot be used for scanning since the light exiting from the fiber diverges, but it can be used in a separate erasure unit.

Lasers of this type are e.g.:

The SDL-7470-P5 laser, that has a power of 3 W. The emission wavelength is 670–690 nm, which is in the useful wavelength range.

Another fiber-coupled laser is the SDL-3400-P6 laser with a power of 16 W.

A third type of fiber-coupled laser is the SDL-6480-P6 laser with a power of 12 W.

A read out apparatus of the above-described kind is commonly used for read out of phosphor screens of a variety of dimensions which are selected for different kinds of applications. However, the dimensions of the read out apparatus and the available possibilities for adjustment of optical and mechanical components imply a maximum format of the screen that can be read out in an apparatus. This maximum format is denoted as $S_{max}$.

The erasure section comprises at least one erasing light source emitting in the range of 300 to 1500 nm. The total electrical power of the erasing unit is preferably not more than 1 Joule multiplied by $S_{max}$ wherein $S_{max}$ is the surface of the largest photostimulable phosphor screen, in $cm^2$, that can be read out in the envisioned read out apparatus.

The wavelength range is selected so as to be optimally matched to the characteristics of the europium activated cesium halide phosphor. The europium activated cesium halide phosphor is most efficiently erased with erasure light within the wavelength range of 500 to 800 nm.

Second Embodiment

Figure 3:
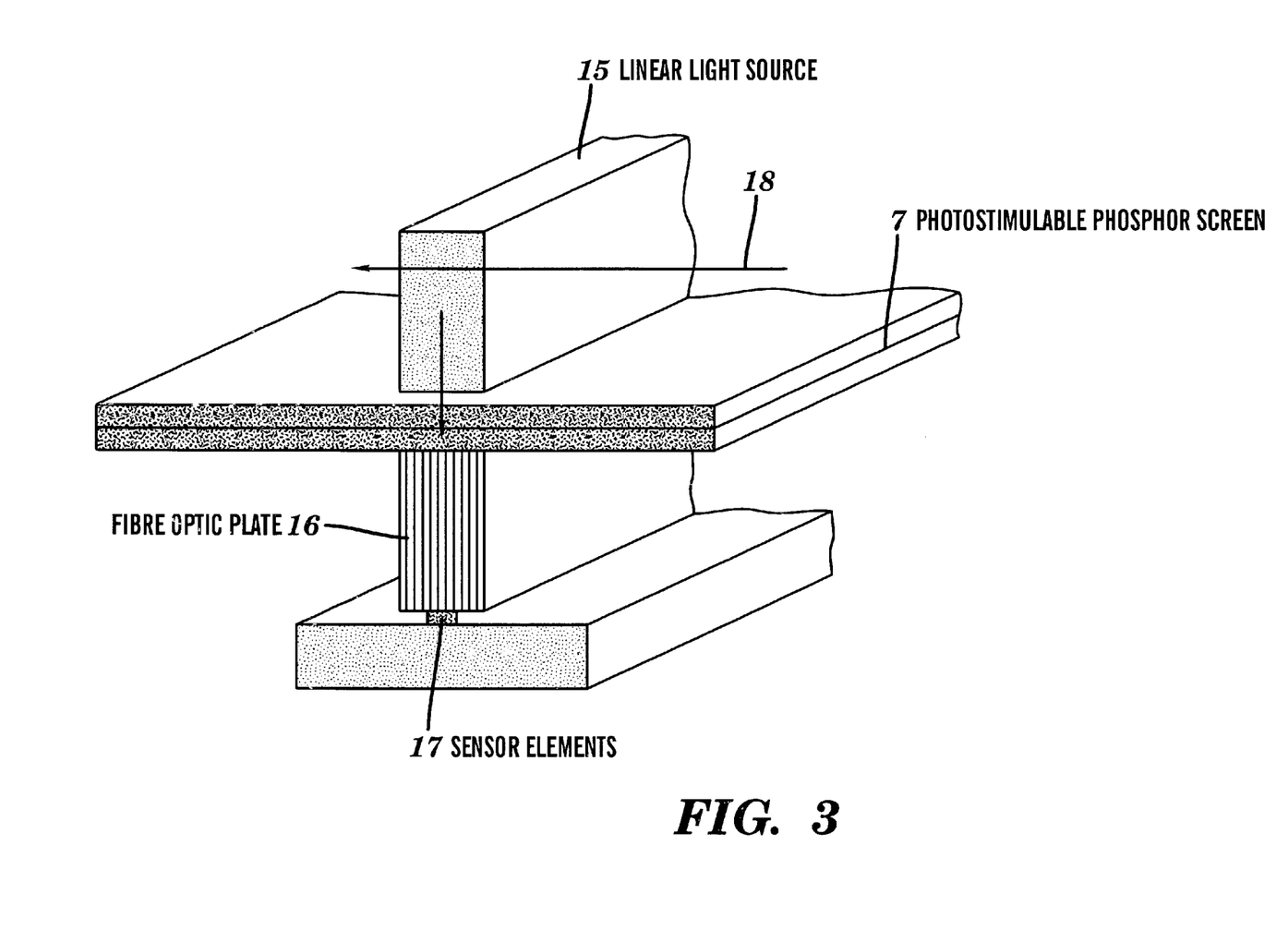
FIG. 3 shows a second embodiment of photostimulable phosphor read out unit, referred to as scan-head type, FIG. 4 schematically shows the position of the stimulating light source and the erasing light source in the embodiment of FIG. 3.

A second embodiment of a read out unit, referred to as scan-head type read out unit type is shown in FIG. 3.

The described scan-head type differs from the conventional flying spot type in that in the scan-head type the image read out is line-wise whereas in the conventional flying spot type read out unit the reading is performed in a point-by-point fashion.

In one embodiment the read out unit comprises a linear light source (15) for emitting stimulating light onto the photostimulable phosphor screen.

This linear light source comprises a number (e.g. 10 to 50) individual laser diodes arranged in a row. This light source provides simultaneous illumination of all pixels of a single line of the photostimulable phosphor screen.

The read out unit further comprises a fibre optic plate (16) for directing light emitted by the phosphor screen upon stimulation onto a linear array of sensor elements (17), more particular charge coupled devices. The fibre optic plate (16) comprises a number of light guiding fibres mounted in parallel arranged so as to guide the light emitted by each individual element of an illuminated line onto a sensor element.

Alternatively, the fibre optic plate can be replaced by an arrangement of selfoc lenses or microlenses. A light guide member might even be avoided.

Alternatives may also be envisaged for the linear light source. This linear light source can be replaced by a 'flying spot' light source. The light emitted by this light source is then deflected by a rotatable polygon mirror onto a scan line on the phosphor screen. In this way one point of this line at the time is illuminated.

In the embodiment shown in FIG. 3 the linear light source is arranged on one side of the phosphor screen, the fibre optic plate and the linear array of sensor elements being arranged on the opposite side. Either of these elements extends in the direction of a scan line.

During read out, the phosphor screen on the one hand and the assembly of fibre optic plate and sensor array on the other hand are displaced relative to each other in the direction of arrow (18).

In still another embodiment which is not shown the array of stimulating light sources, an arrangement of selfoc or microlenses and the sensor array are arranged at the same side of the photostimulable phosphor screen.

After read out the photostimulable phosphor screen is erased so that the energy remaining in the screen after read out is released and so that the screen is in a condition for re-use.

In the type of read out apparatus wherein stimulation is performed by means of light emitted by a linear light source extending parallel to a scan line on the stimulable phosphor screen, the erasure unit preferably forms part of the read out unit.

Figure 4:
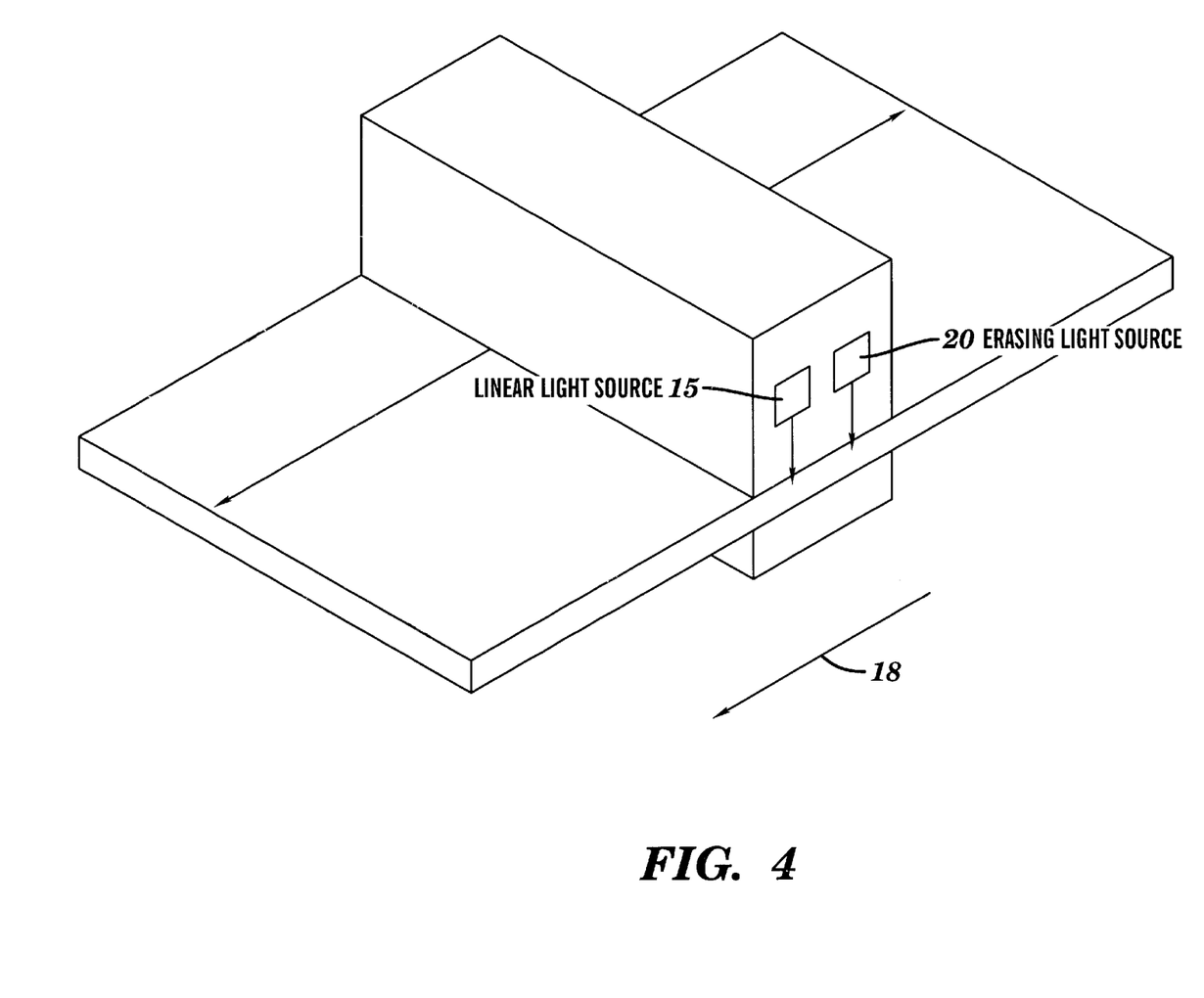

In the embodiment shown in FIG. 3, the erasing light source (20) is part of an assembly comprising the stimulating light source and the light guiding and light detecting means. The position of the stimulating light source and of the erasing light source is shown schematically in FIG. 4.

Preferably the erasing section comprises an erasing light source emitting in the range of 300 nm to 1500 nm and having an electrical power of not more than $1 \text{ J} \times S_{max}$.

Read-out and erasure may take place simultaneously or, alternatively, erasure may start after completion of screen read-out.

In the above-described scanner set-up, the same laser can be used for read-out and erasure. In this case, erasure takes place when read-out is finished and since a powerfull laser must be used to reach a sufficient erasure depth in a short time, the laser must be dimmed during read-out. This can be achieved by using an optical filter, or by reducing the optical power eletronically.

If the same laser is used for read-out and erasure, the laser emitting dimensions must be small, i.e. $3\mu$ or smaller, in one direction.

Lasers of this type are e.g.:

An SDL-3400 laser, that has emitting dimensions of 1 cm×1$\mu$ and a power of up to 20 W.

An SDL-7430 laser has a power of 0.5 W and emits at 680 nm. This laser again can be used in a separate scan unit, but it can be used simultaneously as scanning and erasing laser in a line scanner, because its emitting dimensions are 250× 1$\mu$.

Another type of high power laser is a fiber-coupled laser. This type of laser can be used for erasure, but it cannot be used for scanning since the light exiting from the fiber diverges in 2 dimensions.

Lasers of this type are e.g.:

The SDL-7470-P5 laser, that has a power of 3 W. The emission wavelength is 670–690 nm, which is in the useful wavelength range.

Another fiber-coupled laser is the SDL-3400-P6 laser with a power of 16 W.

A third type of fiber-coupled laser is the SDL-6480-P6 laser with a power of 12 W.

In case read-out and erasure take place in 2 spearate units, the erasing light source assembly is arranged parallel to the linear array of stimulating light sources. Optical separation between read-out unit and erasure unit is necessary in this case and can be achieved as described for the flying-spot scanner. The erasing light source is transported past the image that is read at the same transportation speed in between 30mm/sec and 250 mm/sec. In this way the erasing light source illuminates a line of the image after it has been submitted to read out.

Figure 5:
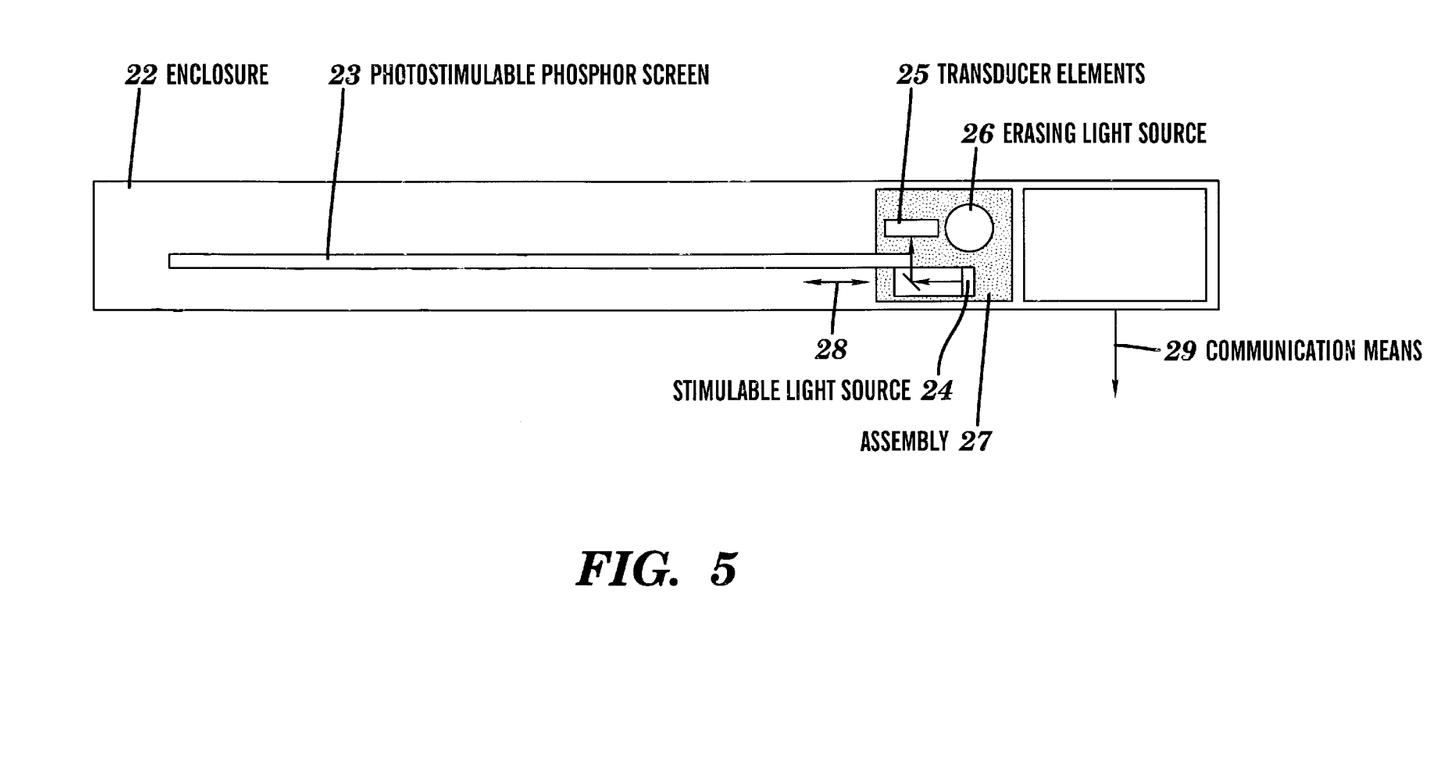
FIG. 5 shows a radiation detector according to the present invention.

Another aspect of the present invention relates to a re-usable radiation detector. This type of detector is shown in FIG. 5.

The detector comprises an enclosure (22). Within the enclosure a photostimulable phosphor screen (23) is located. This screen preferably comprises a divalent cesium halide phosphor, wherein said halide is at least one of chloride and bromide.

The enclosure further comprises a source of stimulating light is (24) arranged for stimulating said phosphor screen and an array of transducer elements (25) for capturing light emitted by the phosphor upon stimulation and for converting said light into an electrical signal representation. In the illustrated embodiment the source of stimulating light is a linear light source and the array of transducer elements is also a linear array. This embodiment can be made very compact and provides fast read out.

The enclosure further comprises an erasing light source (26) arranged substantially parallel to the stimulating light source.

The enclosure still further comprises means (not shown) for transporting the assembly (27) of stimulating light source, erasing light source and array of transducer elements relative to the phosphor screen in a so-called sub-scan direction, indicated by arrow (28).

Means (29), for example an electronic interface and communication channel, are further provided for communicating the electrical signal representation output by the array of transducer elements to an external signal processing device.

In this re-usable radiation detector the phosphor screen remains inside the enclosure during irradiation, read out and erasure.

In this embodiment the stimulating light source and the array of transducer elements are arranged on opposite sides of the phosphor screen.

In alternative embodiment these items may be arranged on the same side of the phosphor screen.

The stimulable phosphor screen in the several embodiments of the present invention comprises a divalent europium activated cesium halide phosphor. Such a phosphor is known in the art and has for example been disclosed in EP-A-174 875 (and U.S. Pat. No. 5,028,509). The phosphor is especially well suited for manufacturing 'binderless' phosphor screens. Binderless phosphor screens provide optimal sharpness.

It is advantageous however to use a CsX:Eu phosphor wherein X represents a halide selected from the group consisting of Br and Cl, which is obtained by the following method:

mixing CsX with between $10^{-3}$ and 5 mol % of a Europium compound selected from the group consisting of $EuX'_2$, $EuX'_3$ and $EUOX'$, X' being a member selected from the group consisting of F, Cl, Br and I, firing the mixture at a temperature above 450° C.

cooling said mixture and recovering the CsX:Eu phosphor.

A phosphor that has been obtained as a result of the above method of preparation has an increased conversion efficiency compared to the state of the art divalent europium activated cesium halide phosphor. The phosphor can be stimulated by means of a lower amount of stimulation energy.

A photostimulable phosphor screen using such a phosphor is preferably obtained by the method of preparing said CsX:Eu phosphor by firing a mixture of said CsX with between 10–3 and 5 mol % of an Europium compound selected from the group consisting of $EuX'_2$, $EuX'_3$ and $EuOX'$, X' being a halide selected from the group consisting of F, Cl, Br and I and applying said phosphor on a substrate by a method selected from the group consisting of physical vapor deposition, thermal vapor deposition, chemical vapor deposition, radio frequency deposition and pulsed laser deposition.

This method of preparation is advantageous because it allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

Alternatively a phosphor screen containing a CsX:Eu stimulable phosphor, wherein X represents a halide selected from the group consisting of Br and Cl can also be manufactured by performing the steps of:

bringing multiple containers of said CsX and an Europium compound selected from the group consisting of $EuX'_2$, $EuX'_3$ and $EuOX'$, X' being a halide selected from the group consisting of F, Cl, Br and I in condition for vapor deposition and depositing, by a method selected from the group consisting of physical vapor deposition, thermal vapor deposition, chemical vapor deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

This method of preparation is advantageous because it likewise allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

This specific phosphor as well as the methods of preparation have been disclosed in U.S. provisional applications No. 60/159,004 and 60/142,276 which are incorporated herein by reference.

Measurements

The erasability of a CsBr:Eu screen was measured in comparison to a commercial MD-10 BaFBr:Eu screen (trade name of Agfa-Gevaert N.V.).

Sample Preparation

The CsBr:Eu screen was produced in the following way:

A CsBr:Eu sample screen was made via thermal vapor deposition of CsBr and the EuOBr. To this aim, CsBr was mixed with EuOBr and placed in a container in a vacuum deposition chamber. The phosphor was deposited on a glass disk with a thickness of 1.5 mm and a diameter of 40 mm. The distance between the container and the substrate was 10 cm. During evaporation, the substrate was rotated at 12 rpm.

The substrate temperature was ca. 200° C. at the start of the evaporation process.

The container was heated to a temperature of 750° C.

Before the start of the evaporation, the chamber was evacuated to a pressure of $4.10^{-5}$ mbar. During the evaporation process, Ar was introduced in the chamber and the Ar gas pressure was $1.6 \cdot 10^{-2}$ mbar.

The resulting screen had a thickness of 850μ.

The Eu-concentration in the evaporated screen was measured with X-ray fluorescence. At the substrate side, the phosphor contained 400 ppm of Eu and at the surface side 800 ppm.

Measurement Procedure

In a first measurement, both screens were homogeneously irradiated with a dose of ca. 50 mR at 80 kVp.

The screens were read out in a flying spot scanner. The scanning light source was a 30 mW diode laser emitting at 690 nm. A 4 mm Hoya BG-39 (trade name) filter was used to separate the stimulation light from the screen emission light. The scan-average levels (SAL's) were determined as the average signal produced by the screens in the photomultiplier tube. The results of these measurements were a $SAL_1$ value for the $CsBr:Eu^{2+}$ screen and a $SAL_1$ value for the MD-10 screen (Table 1).

In a second measurement, the MD-10 screen was homogeneously irradiated with a dose of ca. 44 R, also at 80 kVp.

Next, the screen was erased with a 500 W (electrical power) quartz-halogen lamp for 1 s. The light intensity at the screen position was measured using a photometer and was 12 $mW/cm^2$.

After erasure, the screen was read out with the above-described scanner, and the SAL was measured. This measurement yielded the $SAL_2$ value for the MD-10 screen (Table 1).

Erasure depth, defined as the SAL after erasure divided by the SAL prior to erasure was calculated using the equation:

$$E_d = SAL_2 \times 50/(SAL_1 \times 44{,}000) \quad (1),$$

where the factor 50/44,000 corrects for the difference in dose in the measurements 1 and 2.

In a third measurement, the CsBr:Eu$^{2+}$ screen was homogeneously irradiated with a dose of ca. 166 R, also at 80 kVp.

Next, the screen was erased with the 500 Watt quartz-halogen lamp for 1 s. The light intensity on the screen was, again, 12 mW/cm$^2$.

After erasure, the screen was read out with the above-described scanner, and the SAL was determined. This measurement yielded the SAL$_3$ value for the CsBr:Eu$^{2+}$ screen (Table 1).

Erasure depth, defined as the SAL after erasure divided by the SAL prior to erasure was calculated using the equation:

$$E_d = SAL_3 50/(SAL_1 \times 166{,}000) \quad (2),$$

where the factor 50/166,000 corrects for the difference in dose in the measurements 1 and 3.

TABLE 1

Measured SAL values and calculated $E_d$ values for MD-10 and CsBr:Eu$^{2+}$ screens

|  | MD-10 BaFBr:Eu$^{2+}$ | CsBr:Eu$^{2+}$ |
|---|---|---|
| SAL$_1$ | 440 | 1,180 |
| SAL$_2$ | 2,800 |  |
| SAL$_3$ |  | 290 |
| E$_d$ | 7.10$^{-3}$ | 7.10$^{-5}$ |

It is clear that CsBr:Eu has a much better erasability than the commercial BaFBr:Eu$^{2+}$ phosphor. As a consequence, much less erasure power is needed to erase the CsBr:Eu$^{2+}$ storage phosphor screen and the object of the present invention can be accomplished by making an imaging system based on CsBr:Eu instead of BaFBr:Eu.

In a fourth set of measurements, the CsBr:Eu$^{2+}$ screen was erased with a laser emitting at 685 nm.

The laser beam was expanded to give an intensity of 0.125 mW/cm$^2$ on the screen to be erased.

In a first measurement the screen was homogeneously irradiated with a dose of 48 mR at 80 kVp.

The screen was read out with the abovedescribed scanner, and the SAL was measured. This measurement yielded the SAL$_{41}$ value for the CsBr:Eu screen (Table 2).

Next, the CsBr:Eu screen was homogeneously irradiated with a doses ranging from 167 mR to 115 R and erased with the laser set-up for 1 to 100 s (Table 2).

After erasure, the screen was read out with the above-described scanner, and the SAL was measured. The measurements yielded the SAL$_{42}$ to SAL$_{48}$ values given in Table 2.

Erasure depth, defined as the SAL after erasure divided by the SAL prior to erasure was calculated using the equation:

$$E_d = SAL_{4x} \times 48/(SAL_{41} \times \text{Dose}(x)) \quad (2),$$

wherein the factor 48/Dose(x) corrects for the difference in dose in the measurements.

TABLE 2

Measured SAL values and calculated $E_d$ value for the CsBr:Eu$^{2+}$ screen for monochromatic erasure at 685 nm

| Measurement | X-ray dose (mR) | Erasure time (s) | SAL (V) | E$_d$ |
|---|---|---|---|---|
| 41 | 48 | 0 | 917 | 1 |
| 42 | 167 | 1 | 842 | 2.6 10$^{-1}$ |
| 43 | 167 | 2 | 399 | 1.3 10$^{-1}$ |
| 44 | 234 | 5 | 142.5 | 3.2 10$^{-2}$ |
| 45 | 1,026 | 10 | 95.6 | 4.9 10$^{-3}$ |
| 46 | 25,400 | 20 | 323 | 6.6 10$^{-4}$ |
| 47 | 50,500 | 50 | 53.4 | 5.5 10$^{-5}$ |
| 48 | 115,000 | 100 | 17 | 7.7 10$^{-6}$ |

The results in Table 2 demonstrate that an erasure time of ca. 80s is required in the used set-up to reach the desired erasure depth of 3 10$^{-5}$.

With an erasure intensity of 0.125 mW/cm$^2$, this corresponds to a required erasure power of 10 mW/cm$^2$.

Calculation of the Required Electrical Power

The largest screens that are used in medical radiography have a size of 35×43 cm$^2$, i.e. a size of 1,500 cm$^2$.

As indicated above, an erasure depth of 3.10$^{-5}$ is reached when the CsBr:Eu$^{2+}$ screen is erased with an optical energy of 10 mJ/cm$^2$. The optical energy to erase a complete screen is, therefore: 15 J.

Some high power lasers have emitting dimensions that are small in one direction and large, i.e. 10$\mu$ or larger, in the other direction. This means that these lasers can not be used as a scanning lasers in a flying spot scanner, because it is impossible to focus the scanning laser beam to sufficiently small dimension. The laser can be used, however, in an erasure unit. The laser can be used in a line scanner as well. In this last type of scanner, the laser can be used as scanning device and as erasing device. If the laser is used for scanning and erasing, a filter has to be provided, that reduces the laser power on the phosphor screen while scanning and that is removed while erasing.

Lasers of this type are e.g.:

An SDL-3400 laser, that has emitting dimensions of 1 cm×1$\mu$ and a power of up to 20 W. With this laser the erasure time for a 35×43 cm$^2$ CsBr:Eu screen would be of the order of 1 s or less.

An SDL-7430 laser has a power of 0.5 W and emits at 680 nm. With this type of laser, the CsBr:Eu phosphor can be erased in 30 s. This laser again can be used in a separate scan unit, but it can be used simultaneously as scanning and erasing laser in a line scanner, because its emitting dimensions are 250×1$\mu$.

Another type of high power laser is a fiber-coupled laser. This type of laser cannot be used for scanning since the light exiting from the fiber diverges.

Lasers of this type are e.g.:

The SDL-7470-P5 laser, that has a power of 3 W, which implies an erasure time of ca. 5 s for a 1,500 cm$^2$ CsBr:Eu phosphor screen. The emission wavelength is 670–690 nm, which is in the useful wavelength range.

Another fiber-coupled laser is the SDL-3400-P6 laser with a power of 16 W. This laser will allow to erase the CsBr:Eu phosphor screen in a time of 1 s or less.

A third type of fiber-coupled laser is the SDL-6480-P6 laser with a power of 12 W. This laser will allow to erase the CsBr:Eu phosphor screen in a time of ca. 1.5 s.

What is claimed is:

1. Method of reading a radiation image that has been stored in a photostimulable phosphor screen comprising the steps of (1) stimulating said phosphor screen by means of stimulating radiation emitted by a stimulating light source,
(2) detecting light emitted by the phosphor screen upon stimulation and converting the detected light into a signal representation of said radiation image,
(3) erasing said phosphor screen by exposing it to erasing light, wherein
(4) said photostimulable phosphor screen comprises a divalent europium activated cesium halide phosphor wherein said halide is at least one of chloride and bromide obtained by the following steps:
mixing CsX, wherein X represents a halide selected from the group consisting of Cl and Br, with between $10^{31\ 3}$ and 5 mol % of a Europium compound selected from the group consisting of $EuX'_2$, $EuX'_3$ and $EuOX'$, X' being a member selected from the group consisting of F, Cl, Br and I,
firing the mixture at a temperature above 450° C.,
cooling said mixture, and
recovering the CsX: Eu phosphor, and wherein
(5) said erasing light is emitted by an erasing light source assembly comprising at least one laser.

2. A method according to claim 1 wherein said stimulating light source is the same light source as said erasing light source.

3. A method according to claim 1 wherein said phosphor screen is obtained by the steps of
preparing said CsX:Eu phosphor by firing a mixture of said CsX with between $10^{-3}$ and 5 mol % of an Europium compound selected from the group consisting of $EuX'_2$, $EuX'_3$ and $EuOX'$, X' being a halide selected from the group consisting of F, Cl, Br and I, and
applying said phosphor on a substrate by a method selected from the group consisting of physical vapour deposition, thermal vapour deposition, chemical vapour deposition, radio frequency deposition and pulsed laser deposition.

4. A method according to claim 1 wherein said phosphor screen is obtained by the steps of
bringing multiple containers of said CsX and an Europium compound selected from the group consisting of $EuX'_2$, $EuX'_3$ and $EuOX'$, X' being a halide selected from the group consisting of F, Cl, Br and I in condition for vapour deposition and
depositing, by a method selected from the group consisting of physical vapour deposition, thermal vapour deposition, chemical vapour deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

5. A method for providing a re-usable radiation detector comprising:
stimulating a photostimulable phosphor screen using at least one source of stimulating light;
capturing light emitted by the phosphor screen upon stimulation, and converting the light into an electrical signal representation, using an array of transducer elements;
erasing the screen when it has been read out using an erasing unit;
the stimulating and erasing being obtained by transporting the at least one source of stimulating light, the array of transducer elements, and said erasing unit, relative to the phosphor screen; and
communicating said electrical representation to an external signal processing device;
wherein the photostimulable phosphor screen comprises a divalent europium activated cesium halide phosphor wherein the halide is at least one of chloride and bromide, and wherein the phosphor is obtained by;
mixing CsX, wherein x represents a halide selected from the group consisting of Cl and Br, with between $10^{-3}$ and 5 mol % of a Europium compound selected from the group consisting of $EuX'_2$, $EuX'_3$ and $EuOX'$, X' being a member selected from the group consisting of F, Cl, Br and I,
firing the mixture at a temperature above 450° C.,
cooling said mixture, and
recovering the CsX:Eu phosphor.

6. A method according to claim 5, wherein the erasing unit comprises at least one laser.

7. A method according to claim 5 wherein the stimulating light source is a linear array of laser diodes.

8. A method according to claim 5 wherein the array of transducer elements is a linear array of charge coupled device elements.

9. A method according to claim 5 wherein the phosphor screen is obtained by:
preparing the CsX:Eu phosphor by firing a mixture of the CsX with between $10^{-3}$ and 5 mol % of an Europium compound selected from the group consisting of $EuX'_2$, $EuX'_3$ and $EuOX'$, X' being a halide selected from the group consisting of F, Cl, Br and I; and
applying the phosphor on a substrate by a method selected from the group consisting of physical vapour deposition, thermal vapour deposition, chemical vapour deposition, radio frequency deposition and pulsed laser deposition.

10. A method according to claim 5 wherein the phosphor screen is obtained by:
bringing multiple containers of the CsX and an Europium compound selected from the group consisting of $EuX'_2$, $EuX'_3$ and $EuOX'$, X' being a halide selected from the group consisting of F, Cl, Br and I in condition for vapour deposition; and
depositing, by a method selected from the group consisting of physical vapour deposition, thermal vapour deposition, chemical vapour deposition, electron beam deposition, radio frequency deposition and pulsed laser deposition, both the CsX and the Europium compound on a substrate in such a ratio that on the substrate a CsX phosphor, doped with between $10^{-3}$ and 5 mol % of an Europium compound, is formed.

* * * * *

UNITED STATES PATENT AND TRADEMARK OFFICE
Certificate

Patent No. 6,512,240 B1                                                                 Patented: January 28, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul Leblans, Kontich, Belgium; Luc Struye, Mortsel, Belgium; Martin Devenney, Mountain View, CA; and Casper Reaves, San Jose, CA.

Signed and Sealed this Sixth Day of July 2004.

GEORGIA Y. EPPS
*Supervisory Patent Examiner*
Art Unit 2873